United States Patent [19]

Chin

[11] Patent Number: 5,391,182
[45] Date of Patent: Feb. 21, 1995

[54] APPARATUS AND METHOD FOR CLOSING PUNCTURE WOUNDS

[75] Inventor: Albert K. Chin, Palo Alto, Calif.

[73] Assignee: Origin Medsystems, Inc., Menlo Park, Calif.

[21] Appl. No.: 100,926

[22] Filed: Aug. 3, 1993

[51] Int. Cl.⁶ .............................................. A61B 17/04
[52] U.S. Cl. ................................. 606/213; 606/215; 606/144; 604/15; 604/288; 128/898
[58] Field of Search .................... 606/144–148, 606/139, 224, 213, 215; 128/898, 899; 604/15, 52, 60, 168, 288, 285

[56] References Cited

U.S. PATENT DOCUMENTS

| 4,493,323 | 1/1985 | Albright et al. | 606/144 |
|---|---|---|---|
| 4,669,473 | 6/1987 | Richards et al. | 606/215 |
| 4,744,364 | 5/1988 | Kensey | 606/213 |
| 5,021,059 | 6/1991 | Kensey | 606/213 |
| 5,053,046 | 10/1991 | Janese | 606/215 |
| 5,061,274 | 10/1991 | Kensey | 606/213 |
| 5,085,661 | 2/1992 | Moss | 606/139 |
| 5,171,259 | 12/1992 | Inoue | 606/213 |
| 5,222,508 | 6/1993 | Contarini | 128/898 |
| 5,257,637 | 11/1993 | El Gazayerli | 606/139 |
| 5,281,234 | 1/1994 | Wilk et al. | 606/139 |
| 5,282,827 | 2/1994 | Kensey et al. | 606/215 |
| 5,320,632 | 6/1994 | Heidmuller | 606/144 |

OTHER PUBLICATIONS

Product Literature for: "The ENDO-JUDGE" Synergistic Medical Technologies, Inc., 1994.
Product Literature for: "FLEXIFLO T-Fastener Set", Jan. 1993.

Primary Examiner—Tamara L. Graysay
Assistant Examiner—Gary Jackson
Attorney, Agent, or Firm—Limbach & Limbach

[57] ABSTRACT

An apparatus for suturing fascial tissue for deep puncture wounds utilizes a flexible membrane inserted into a body cavity through a trocar sheath positioned in a wound. A suture to be applied to the wound has anchors attached to each of its ends. A pair of suture-carrying needles each carry an end of the suture and its corresponding anchor. The suture-carrying needles are passed through the fascial layer surrounding the wound and are subsequently passed through the flexible membrane. The suture ends and corresponding anchor means are released from the needles. A lifting force is applied to the flexible member via a cord or shaft which extends out of the wound. The anchors are engaged by the flexible membrane as it is withdrawn out of the wound, pulling the ends of the suture out of the wound to close the opening in the fascial tissue.

21 Claims, 7 Drawing Sheets

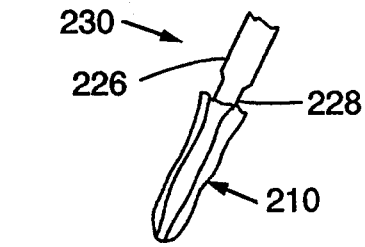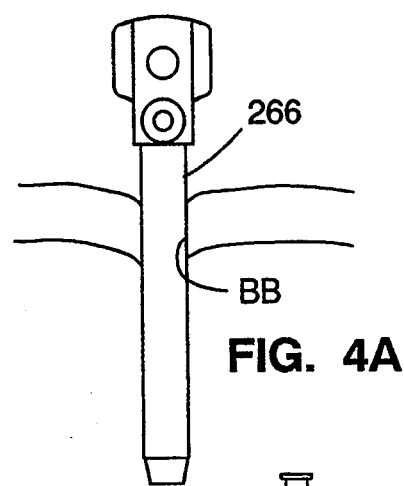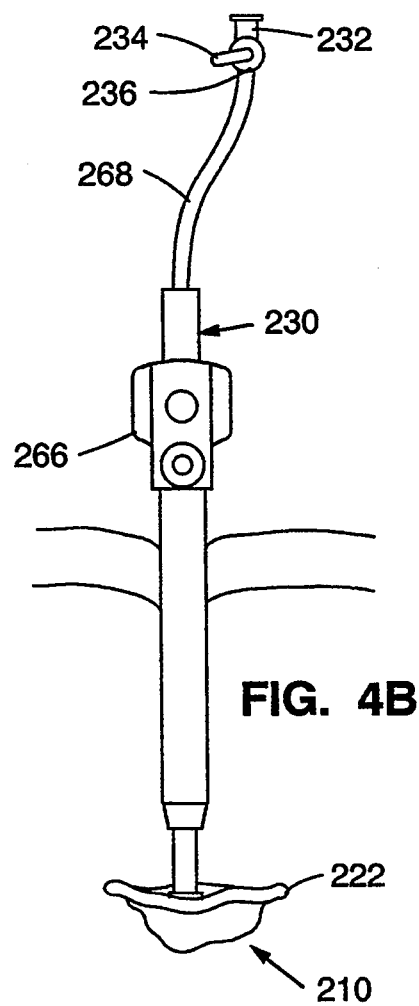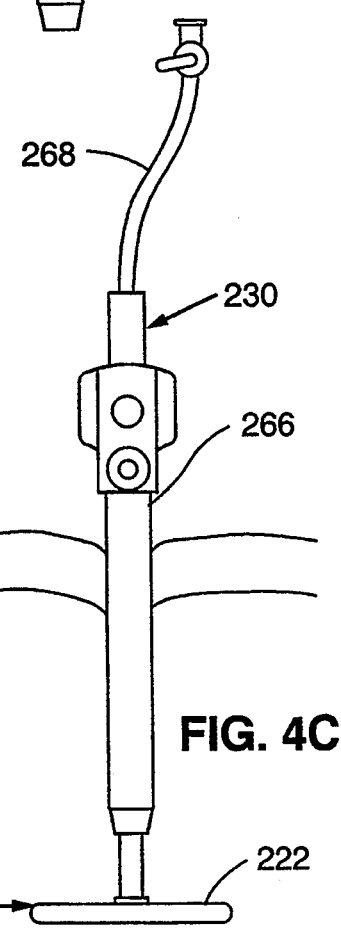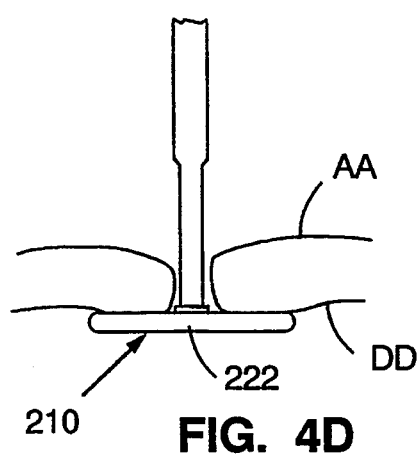
FIG. 4A
FIG. 4B
FIG. 4C
FIG. 4D

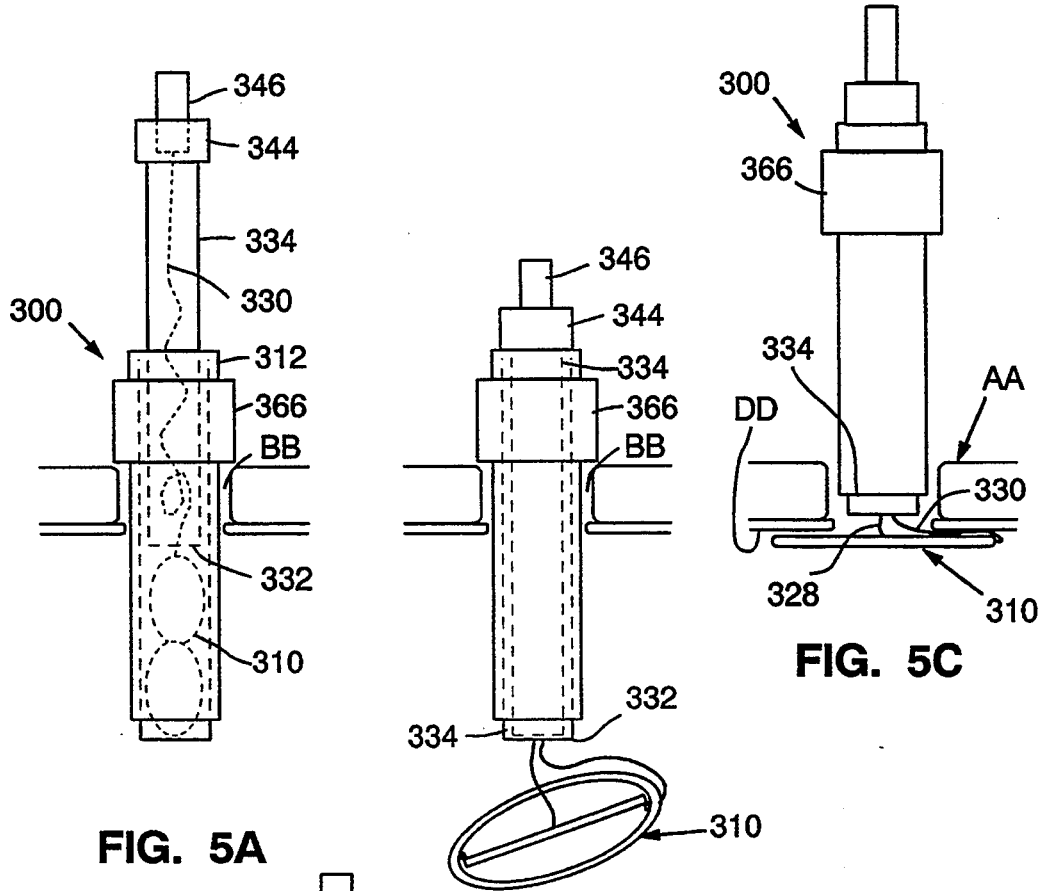
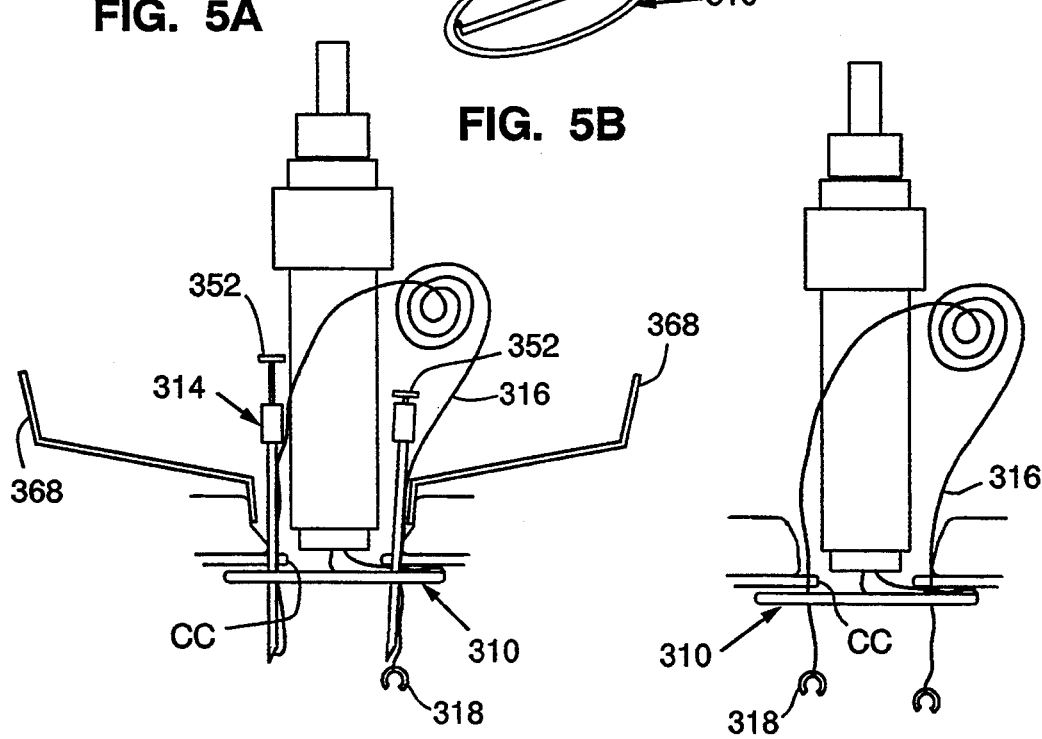
FIG. 5A
FIG. 5B
FIG. 5C
FIG. 5D
FIG. 5E

5,391,182

APPARATUS AND METHOD FOR CLOSING PUNCTURE WOUNDS

FIELD OF THE INVENTION

The present invention relates to the field of surgical instruments and particularly to instruments for use in applying sutures to deep wounds.

BACKGROUND OF THE INVENTION

For laparoscopic surgery, pointed surgical instruments, called trocars, are used to provide access to body cavities by creating puncture openings through the abdominal wall. Laparoscopic surgery often requires trocar punctures measuring 10 mm in diameter or larger. These punctures can only adequately be closed using suture closure of the fascia, the thick fibrous layer of tissue which lies between the muscle and the peritoneum. If the fascia is not properly sutured, the peritoneum and bowel may begin to protrude through the fascial opening, a condition called postoperative incisional hernia.

The most common method for closing these puncture openings utilizes a curved suture needle. The skin, subcutaneous fat, and muscle are retracted away from the puncture opening and the fascia is identified. The curved needle and the attached suture are passed through the fascia on one side of the puncture opening, through the abdominal cavity, and back through the fascia on the opposite side of the puncture opening. The ends of the suture are subsequently pulled closed and tied to close the puncture opening.

While frequently successful, complications may arise from the use of this method. If the patient is obese, several inches of subcutaneous fat must be retracted away in order for the fascia to be isolated. The thick layer of fat causes the fascial tissue through which the needle is to be inserted to be recessed several inches from the exterior of the abdominal wall, making manipulation of the needle between the thick walls of fat and tissue difficult. Because the procedure involves passing the needle into the abdomen, poor control of the needle may result in puncture of the underlying bowel or inadvertent incorporation of the bowel into the fascial closure.

Two other devices have also been used for fascial closure. One, the REMA device, comprises a long member which is inserted into the puncture hole with its distal end positioned in the abdominal cavity. Once the distal end of the long member is inside the abdominal cavity, a pair of needle-carrying members are extended laterally from the long member. The needle-carrying members hold two needles with their pointed needle tips directed towards the interior surface of the abdominal wall, such that the axes of the needles are parallel to the axis of the long member. Each needle carries one end of a single suture. The long member is then pulled outward of the puncture hole in a longitudinal direction, causing the tips of the suture-carrying needles to advance through the abdominal wall and out of the body. A needle-clamping device is advanced towards the suture-carrying needles, engages with the needles and removes them from the abdominal wall. The suture ends are removed from the needles and tied off, the needles are retracted by the needle-carrying member, and the apparatus is removed from the abdominal cavity via the puncture hole.

The suture tie applied by the REMA device passes through the entire abdominal wall, including the skin, fat, and muscle. Necrosis of the skin and muscle tissue may occur because of the strongly tensioned suture tie that is required to close the strong and fibrous fascial layer. Moreover, because the REMA needles pass outwardly through the skin from the abdominal cavity, the device exposes the surgeon to the risk of being injured by the blind passage of sharp needles through the abdominal wall.

Another method involves inserting a suture through fascial tissue using a needle, retrieving the suture from the needle inside the abdominal cavity using a grasper, withdrawing the needle and reinserting it at a second location, passing the suture from the grasper to the needle inside the abdominal cavity, and withdrawing the needle with the suture attached. While this method satisfactorily sutures the opening, transfer of the suture between the needle and the grasper requires visualization inside the abdominal cavity, and thereby requires an additional trocar opening for insertion of a laparoscope. An additional closure method is thus needed for closing the trocar puncture used for the laparoscope.

OBJECTS AND SUMMARY OF THE INVENTION

It is an object of the present invention to provide an apparatus and method for performing suture closure of openings in the fascial layer.

The apparatus and method of the present invention provide a technique for threading the ends of a suture into the body through the fascial tissue surrounding a puncture opening or wound and for looping the ends out of the body through the wound so as to create a suture loop which, upon tightening, reapposes the fascial tissue. The invention utilizes a flexible membrane which is inserted through a trocar sheath positioned in the wound and into the body cavity underlying the wound. Once inside the body cavity, the flexible membrane receives the ends of a suture passed through the tissue surrounding the wound and is withdrawn out of the wound, carrying the ends of the suture out of the wound to tighten the suture and close the opening in the tissue.

DETAILED DESCRIPTION OF THE DRAWINGS

FIGS. 4A through 4J are a sequence of side elevational views showing the use of the preferred fascial closure device according to the present invention.

FIGS. 5A through 5H are a sequence of side elevational views showing the use of an alternate embodiment of a fascial closure device according to the invention.

FIG. 8 is a partial cross-sectional side view of the needles according to the invention, showing the alternate embodiment of the anchors positioned in the needles.

DETAILED DESCRIPTION OF THE INVENTION

The preferred embodiment of the fascial closure device is shown in FIGS. 1 through 4J. The apparatus is generally comprised of a suture receiving component 200 and a suture delivering component 202.

Figure 1:
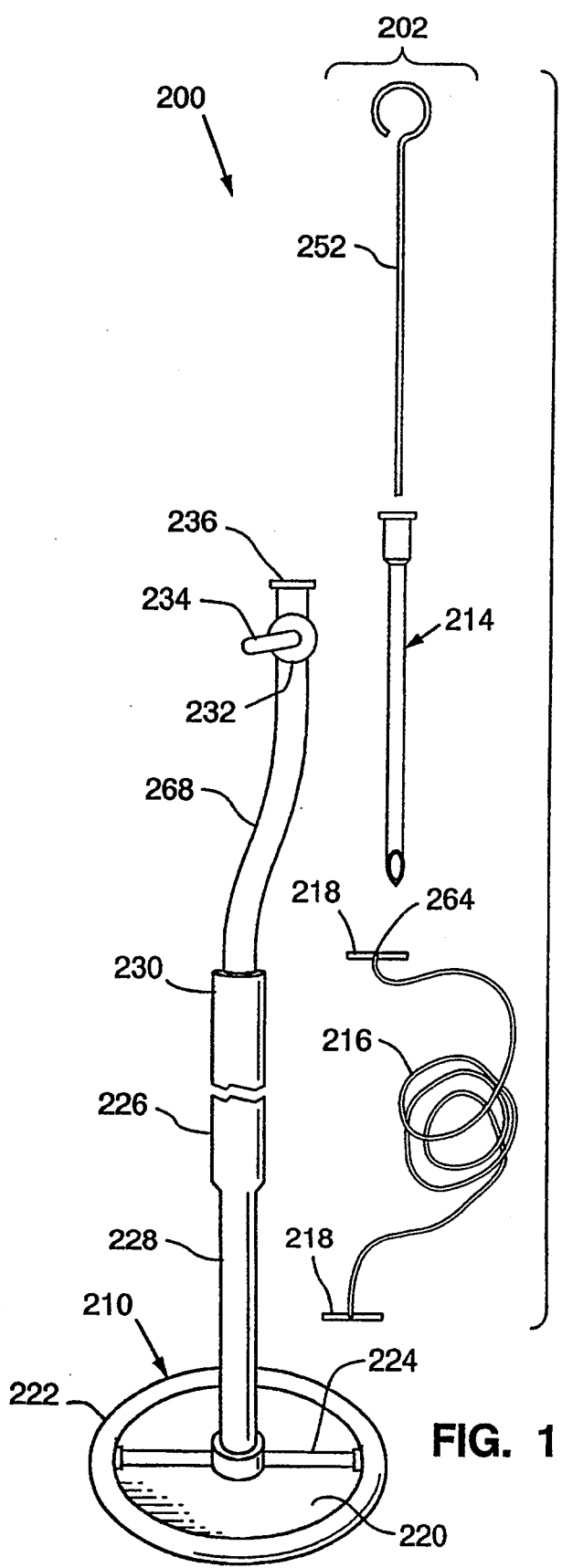
FIG. 1 is a perspective view of the various components of the preferred embodiment of the fascial closure device of the present invention.

The suture receiving component 200 is comprised of a flexible membrane 210 which is preferably a circular disk 220 of elastomeric material. The flexible membrane ideally possesses three properties. It is deformable for insertion into and removal from a trocar sheath 266 (FIG. 4A), sufficiently resilient to resume its relatively flat shape after it has been deformed, and thin enough to be penetrable by a needle tip. These properties are achieved in the preferred embodiment by constructing the flexible membrane as shown in FIG. 1. The circular disk 220 is constructed from a thin elastomeric material. An inflatable ring 222 of elastomeric material lines the perimeter of the disk 220 to increase its resiliency. An inflatable tube 224 divides the disk 220 at its diameter. Each end of inflatable tube 224 provides a passage through which inflation medium (not shown) is passed into inflatable ring 222 as will be described below.

A hollow shaft 226 connects with inflatable tube 224, providing a conduit through which inflation medium may be passed into inflatable tube 224 and inflatable ring 222. The shaft 226 is comprised of narrow portion 228 having a preferred diameter of approximately 5 mm and an increased diameter portion 230 having a preferred diameter of approximately 10 mm. A tube 268 connects the shaft 226 with an inflation port 232 which has a valve 234 and a connector 236 for connecting the shaft 226 to a source of inflation medium.

Figure 2:
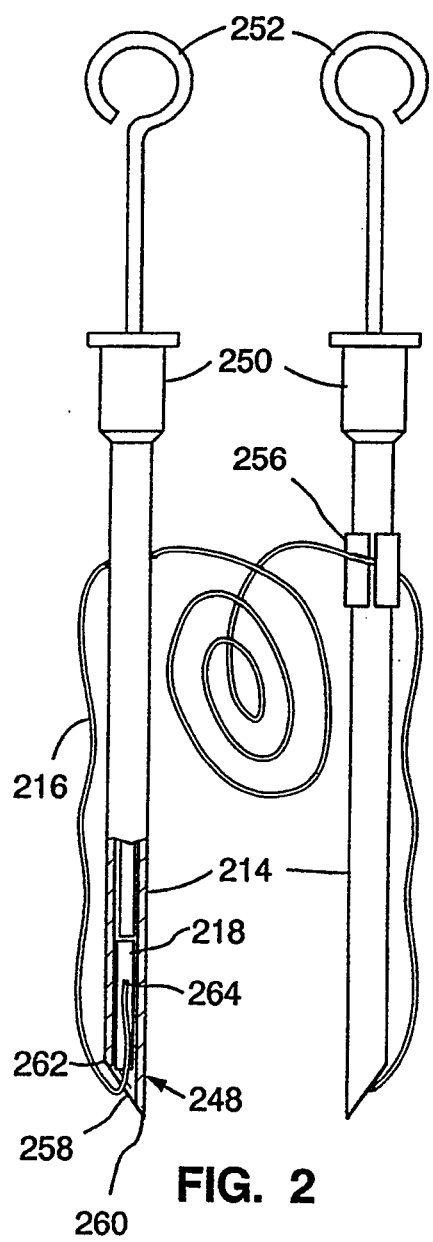
FIG. 2 is a partial cross-sectional side view of the needles of to the present invention.

Referring to FIG. 2, the present invention preferably provides a pair of hollow needles 214 which carry anchors 218 that are attached to each end of a suture 216. The needles 214 each have a throughbore, and are open at their the distal ends 248 and proximal ends 250. Each of the anchors 218 is carried in the throughbore of one of the needles, close to the distal ends, designated 258, of the needles 214. Plungers 252, preferably in the form of stylets, are positioned in the needle throughbores at the proximal ends 250 of the needles. When the plungers 252 are depressed, they travel longitudinally in the needle throughbores in a distal direction, forcing the anchors out of the distal ends of the needle throughbores.

The portions of the suture which are adjacent to the anchors 218 extend longitudinally along the exterior surface of the needles and tuck into split sleeves 256 located near the proximal ends 250 of the needles. The split sleeves 256 hold the suture in place but are capable of releasing the suture when a tensile force is applied to the suture, such as when an anchor is forced out of the needle throughbore by a plunger.

Figure 3:
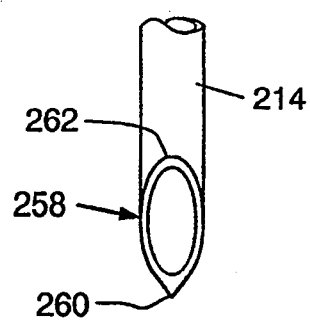
FIG. 3 is a side elevational view of a needle tip of the invention.

As shown in FIG. 3, the ends 258 of the needles 214 are beveled to form a sharp point 260 and a dull short side 262. The short side is dulled to prevent the suture from being cut by the needle tip.

The preferred anchors 218 for use with the present invention are shown in FIGS. 1 and 2. The anchors 218 are tubes that are preferably formed from stainless steel. Each has a hole 264 midway of its length. An end of the suture 216 is positioned in each hole and the tube is crimped down around it to form a swaged connection.

When allowed to hang freely from the suture 216, the anchors 218 assume a substantially horizontal state.

Figure 4E:
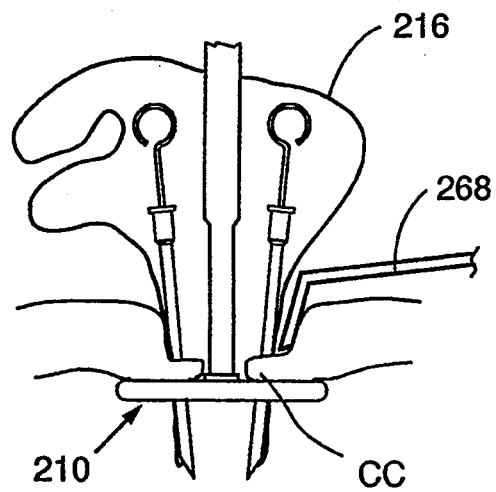

Use of the preferred embodiment will next be described with reference to FIGS. 4A to 4J. A trocar sheath 266 is positioned in a wound opening BB and the flexible membrane 210 is gathered around the narrow portion 228 of the shaft 226 as shown in FIG. 4A. The flexible membrane 210 is pushed through the trocar sheath 266 and into the abdominal cavity as shown in FIG. 4B. The increased diameter portion 230 of the shaft creates a leakproof seal against the trocar sheath to prevent escape of insufflation gas if gas insufflation is used for abdominal distension. A source (not shown) of inflation medium, such as air, is connected to the connecter 236 at inflation port 232. The valve 234 is opened and the inflatable ring 222 and inflatable tube 224 (FIG. 1) are allowed to inflate. The trocar sheath 266 is removed from the site by sliding it along the tube 268 which connects the shaft 226 to the source of inflation medium.

Referring to FIG. 4D, the flexible membrane 210 is next pulled up against the peritoneal surface DD of the abdominal wall AA. Standard retractors 268 are used to retract the skin, subcutaneous fat, and muscle away from the puncture opening, leaving the fascial layer CC exposed as in FIG. 4E.

Figure 4F:
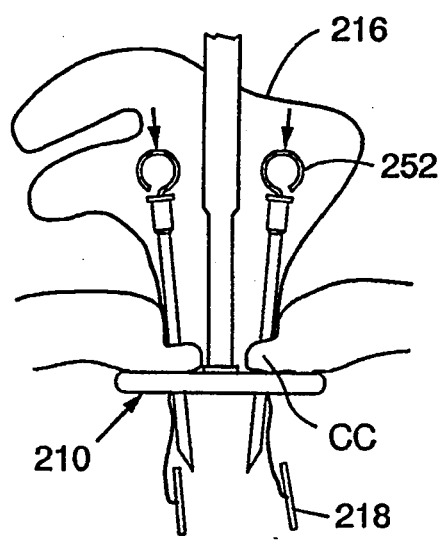
Figure 4G:
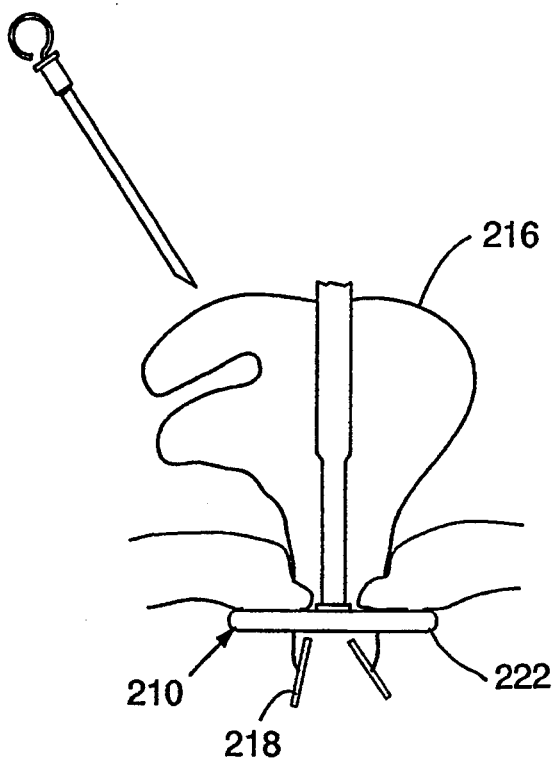

Each anchor 218 is connected to one end of a suture 216 and inserted into the distal end of one of the needles 214. As shown in FIG. 2, the sections of the suture adjacent to the anchors are next curved around the blunt end of the needle and secured by the split sleeves 256. Referring to FIG. 4F, the needles are inserted through the fascial tissue CC exposed by the retractors 268 on opposite sides of the puncture opening and are further advanced through the flexible membrane 210. The plungers 252 are then depressed, causing the anchors 218 to be ejected from the needles by the distal ends of the plungers 252. The force imposed on the suture by the plungers disengages the suture 216 from the split sleeves. The needles are removed leaving the suture ends and anchors hanging into the abdominal cavity as shown in FIG. 4G.

Figure 4H:
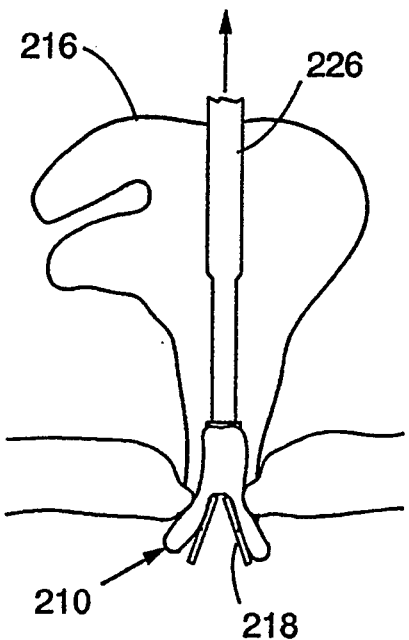
Figure 4I:
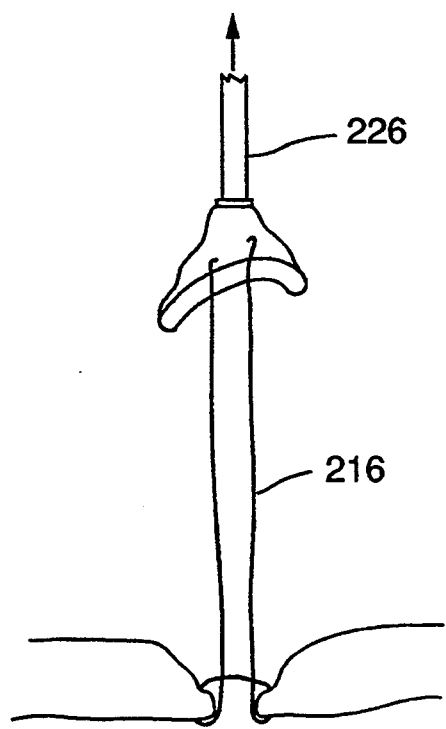
Figure 4J:
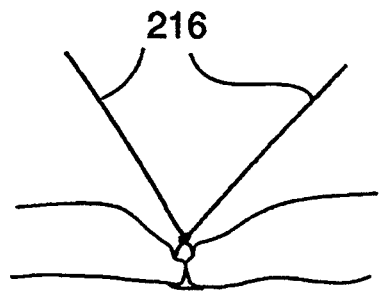

The valve 234 is next opened to allow the inflation medium to release from the inflatable ring 222 and inflatable tube 224. As shown in FIG. 4H, the shaft 226 is pulled in the proximal direction, drawing the flexible membrane out of the wound. The anchors 218, which cannot pass through the flexible membrane 210, are carried by the flexible membrane out of the wound causing the tension in the suture to increase and to thereby pull the sutured portions of the fascial tissue closed (FIG. 4I). The suture is then clipped and tied in a knot, as shown in FIG. 4J.

Figure 5F:
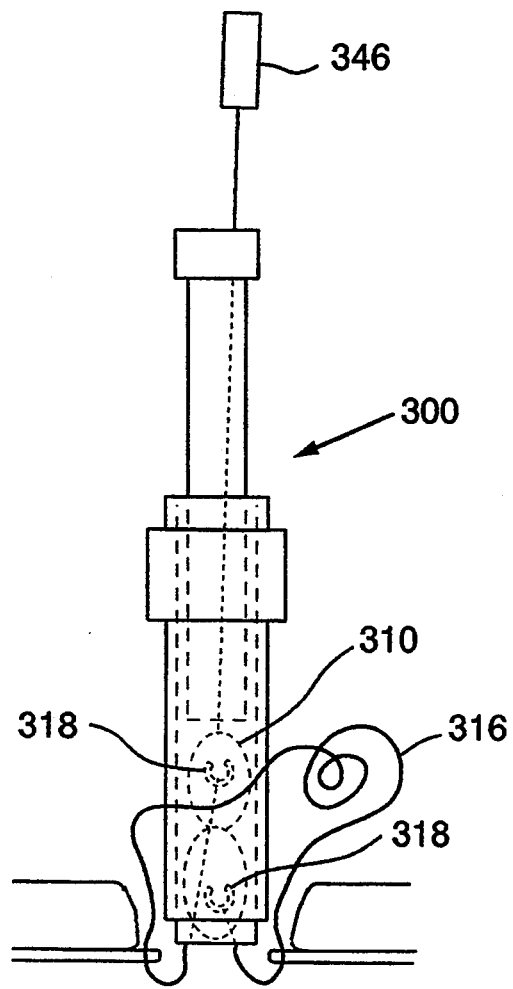
Figure 5G:
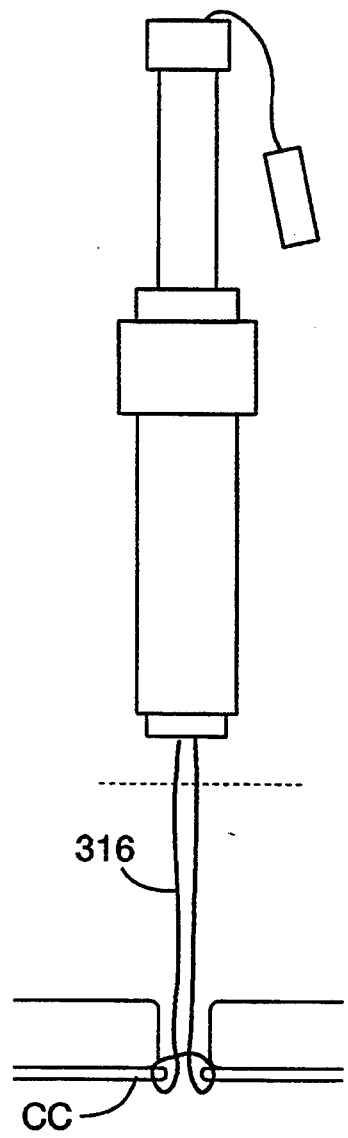
Figure 5H:
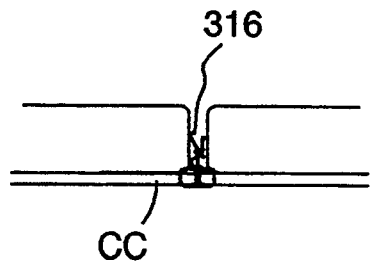
Figure 6:
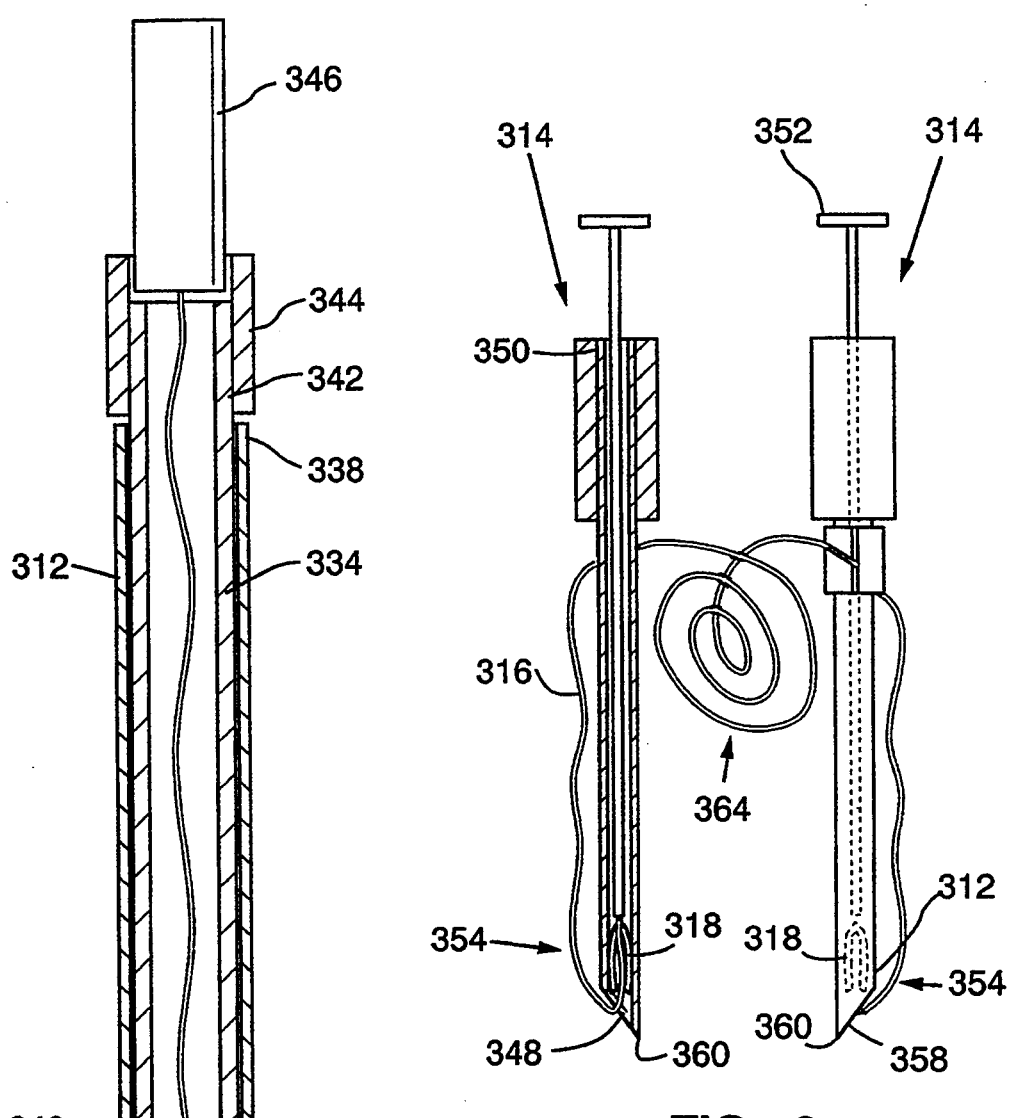
FIG. 6 is a partial cross-sectional side view of the insertion assembly of the alternate embodiment.
Figure 6:
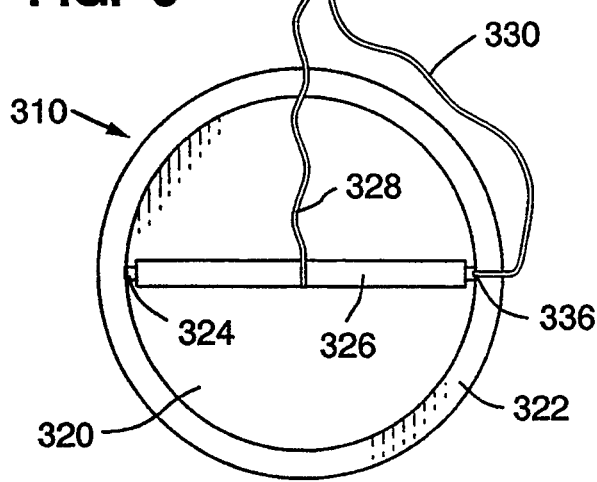

FIGS. 5A through 8 show an alternate embodiment of the fascial closure device. The alternate embodiment is generally comprised of a hollow sheath 312, a flexible membrane 310 capable of passing through a throughbore in the hollow sheath 312, a pair of needles 314 which carry the ends of a suture 316 and anchors 318 attached to each end of the suture 316. As shown in FIG. 6, the circular disk 320 is constructed from a thin elastomeric material. A thickened lip 322 of elastomeric material lines the perimeter of the disk 320 to increase its resiliency. An elastomer crosspiece 324 surrounded by a rigid tubular cross-member 326 divides the disk 320 at its diameter.

Two cords, a central cord 328 and a reinversion cord 330 are attached to the flexible member 310. The cords are made from inelastic line or string such as suture. The central cord 328 is attached at one end to the center of the tubular cross-member 326 and at the other end to a distal end 332 of an insertion tube 334 as will be discussed below. The reinversion cord 330 is attached to the lip 322 at a point 336 where the elastomer crosspiece 324 intersects with the lip 322. These cords are instrumental in moving the flexible membrane in and out of the wound as will be described below.

The concentrically positioned sheath 312 and insertion tube 334 operate with the cords 328, 330 to move the flexible membrane. The sheath 312 has a proximal end 338 and a distal end 340, both of which are open. The insertion tube 334 is positioned in the throughbore of the sheath 312 and is slidable within the sheath in a longitudinal direction. Connected to the distal end 332 of the insertion tube 334 is the central cord 328 which, as described above, is also attached to the rigid tubular cross-member 326 of the flexible membrane 310. The proximal end 342 of the insertion tube 334 protrudes slightly from the proximal end 338 of the sheath and includes a collar 344 which prevents the insertion tube 334 from sliding completely through the sheath 312.

The collar 344 also serves as a seat for a knob 346 which is removably positioned on the collar. The knob 346 is attached to one end of the reinversion cord 330, which passes through the throughbore of the insertion tube and attaches to the lip 322 of the flexible membrane 310 as described above.

Figure 7:
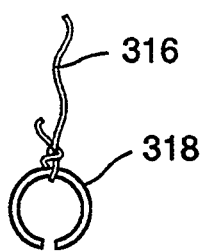
FIG. 7 is a side elevational view of an alternate embodiment of an anchor according to the present invention.

The anchors 318 attached to the ends of the suture 316 are designed to be carried by the needles through the flexible membrane and to expand once released by the plungers. As shown in FIG. 7, an alternative form of anchors comprises flexible split elastomer rings which are inserted into the hollow needles in a compressed state, as in FIG. 8, and which expand once they are released from the hollow needles, as in FIG. 5D.

The use of the alternate embodiment will next be described. For use, the flexible membrane 310 must be positioned inside the sheath 312 as shown in FIG. 5A. To withdraw the flexible membrane into the sheath, the knob 346 is first removed from the collar 344 and pulled in the proximal direction. This causes the point of attachment 336 between the reinversion cord 330 and the lip 322 to pivot around the point of attachment between the central cord 328 and the tubular cross-member 326 and pulls the flexible membrane 310 towards the distal ends of the sheath 312 and the insertion tube 334. The flexible membrane 310 is thereby drawn into the sheath 312. The flexible membrane 310 pushes against the distal end 332 of the insertion tube 334, causing the insertion tube 334 to slide proximally inside the stationary sheath 312. The knob is replaced in the collar as shown in FIG. 5A.

The entire insertion assembly 300, comprising of the sheath 312, insertion tube 334, the knob 346, and the flexible membrane 310, is inserted into a trocar sheath 366 positioned in the wound BB as shown in FIG. 5A. As depicted in FIG. 5B, the insertion tube 334 is next moved in the distal direction such that the distal end 332 of the insertion tube pushes the flexible membrane 310 out of the sheath and into the body cavity underlying the wound BB.

Referring to FIG. 5C, the insertion assembly 300 and the trocar sheath are lifted partially out of the puncture opening such that the flexible membrane 310, which is connected by the central cord 328 to the distal end of the insertion tube 334, is pulled up against the peritoneal surface DD of the abdominal wall AA. Standard retractors 368 are used to retract the skin, subcutaneous fat, and muscle away from the puncture opening, leaving the fascial layer CC exposed as in FIG. 5D. The needles are passed through the fascial layer CC and the flexible membrane 310 as described above and the anchors 318 are released from the needles 314.

Once released the anchors unfold into their expanded state. As in FIG. 5F, the knob 346 is removed from the collar 344 and pulled in the proximal direction, drawing the flexible membrane into the sheath as described earlier. The anchors 318 which cannot pass through the flexible membrane 310, are carried by the flexible membrane into the sheath. The entire insertion assembly 300 is lifted out of the puncture opening as shown in FIG. 5G, causing the tension in the suture to increase and to thereby pull the sutured portions of the fascial tissue closed. The suture is then clipped and tied in a knot, as shown in FIG. 5H.

CONCLUSION

While two embodiments of the present invention have been described, many others are possible according to the present invention. The scope of the present invention is not intended to be limited to the specific embodiment described above; it should be defined by the claims recited below.

I claim:

1. An apparatus kit for closing a wound comprising:
    a suture having at least two ends;
    a suture receiving means for insertion through the wound and into a body cavity underlying the wound;
    a needle means for carrying the ends of the suture through tissue surrounding the wound and to the suture receiving means;
    anchoring means attached to the ends of the suture, for passage through the tissue by the needle means, and for anchoring the suture ends to the suture receiving means while within the body cavity;
    withdrawing means for engaging the suture-receiving means inside the body cavity and for withdrawing the suture-receiving means, with the anchoring means and the suture ends attached thereto, through the wound and out of the body cavity.

2. An apparatus kit for closing a wound with a suture having at least two ends, the apparatus comprising:
    a suture having at least two ends;
    a suture receiver having a flexible membrane capable of being penetrated by a needle, the suture receiver insertable through the wound and into a body cavity underlying the wound and for carrying the ends of the suture out of the wound;
    a needle means for carrying the ends of the suture through tissue surrounding the wound and through the flexible membrane of the suture receiver;
    anchoring means attached to the ends of the suture, for anchoring the suture ends to the suture receiver while within the body cavity;
    withdrawing means for withdrawing the suture receiver with the anchor means and the ends attached thereto, through the wound and out of the body cavity.

3. The apparatus of claim 2 further comprising insertion means for inserting the flexible membrane through the wound and into the body cavity.

4. The apparatus of claim 3 wherein the insertion means comprises:

a first tube capable of being inserted into the wound, the first tube having a first throughbore for receiving the flexible membrane;

a pusher means for insertion into the first throughbore and for pushing the flexible membrane through the first throughbore.

5. The apparatus of claim 4 wherein the pusher means comprises:

a second tube slidably positioned in the first throughbore, the second tube having a proximal end, a distal end and a second throughbore.

6. The apparatus of claim 5 wherein: the withdrawing means comprises:

a knob removably positioned in the second throughbore at the proximal end of the second tube;

a cord passing through the second throughbore, the cord having a first end attached to the flexible membrane and a second end attached to the knob.

7. The apparatus of claim 3 wherein the withdrawing means and the insertion means comprise a shaft connected to the flexible membrane.

8. The apparatus of claim 7 wherein:

the shaft includes a throughbore, a distal end, a proximal end, and an inflation port connected to the proximal end; and the flexible membrane further comprises an inflatable portion having an opening connected to the distal end of the shaft such that an inflation medium introduced into the inflation port inflates the inflatable portion.

9. The apparatus of claim 2 wherein: the needle means comprises:

a hollow needle having a needle throughbore capable of receiving the anchoring means; and plunger means positioned in the needle throughbore, for ejecting the anchoring means from the needle throughbore after the needle has been passed through the flexible membrane.

10. The apparatus of claim 9 wherein each anchoring means comprises a flexible member, the flexible member having a retracted position wherein the flexible member is capable of being positioned inside the needle throughbore and an expanded position wherein the flexible member is incapable of passing through the flexible membrane.

11. The apparatus of claim 9 wherein each anchoring means comprises a tube having first and second ends and wherein the suture ends are connected to the tubes at a point between the first and second ends.

12. A method of closing a wound with a suture, the method comprising the steps of:

providing a suture receiver and a suture having at least two ends;

inserting the suture receiver into the body cavity through the wound;

passing the ends of the suture through tissue surrounding the wound and into a body cavity;

engaging the suture ends with the suture receiver; and withdrawing the ends of the suture out of the body cavity and out of the wound by withdrawing the suture receiver with the suture ends engaged thereto out of the body cavity and out of the wound.

13. A method of closing a wound with a suture, the method comprising the steps of:

providing a suture receiver, a suture having at least two ends, and anchors attached to the ends of the suture;

inserting the suture receiver into a body cavity through the wound;

passing the ends of the suture with the anchors thereon through tissue surrounding the wound and into the body cavity;

engaging the anchors with the suture receiver;

withdrawing the ends of the suture out of the body cavity and out of the wound by withdrawing the suture receiver with the anchors engaged thereto out of the body cavity and out of the wound.

14. The method of claim 13 wherein:

the providing step provides a suture receiver having a flexible membrane, anchors each having a first state wherein the anchors are capable of passing through the flexible membrane and a second state wherein the anchors are incapable of passing through the flexible membrane, and further provides at least two needles capable of carrying the anchors in their first state with the ends of the suture attached thereto;

the passing step includes the step of inserting the hollow needles with the anchors and the ends thereon through the tissue surrounding the wound, through the flexible membrane, and into the body cavity; and the engaging step includes the steps of:

releasing the anchors with the ends thereon from the hollow needles, and allowing the anchors to adjust from their first state to their second state.

15. The method of claim 14 wherein: the providing step further provides:

a first tube having a proximal end, a distal end, and a first throughbore, a second tube having a second throughbore, a proximal end, and a distal end, the second tube slidably positioned in the first throughbore near the proximal end of the first tube, and a line having a first end attached to the distal end of the second tube and a second end attached to the flexible membrane;

the step of inserting the suture receiver into the body cavity through the wound includes the steps of:

positioning the flexible membrane inside the first throughbore distally from the second tube, inserting the distal end of the first tube into the wound, and sliding the second tube in a distal direction within the first throughbore thereby ejecting the flexible membrane through the distal end of the first tube and into the abdominal cavity.

16. The method of claim 15 wherein:

the providing step further provides a cord having a first end and a second end connected to the flexible membrane; and the withdrawing step includes the step of:

applying a lifting force to the first end, thereby lifting the flexible membrane out of the wound and into the first tube.

17. The method of claim 14 wherein:

the providing step further provides a shaft having a proximal end and a distal end connected to the flexible membrane; and the step of inserting the suture receiver into the body cavity through the wound includes the steps of:

positioning the flexible membrane over the wound; and delivering a pushing force to the shaft to push the flexible membrane into the wound.

18. The method of claim 14 wherein:

the providing step further includes a shaft having a proximal end and a distal end connected to the flexible membrane; and the withdrawing step includes the step of:

applying a lifting force to the proximal end of the shaft, thereby lifting the flexible membrane out of the wound.

19. The method of claim 17 or 18 wherein:

the providing step further provides an inflatable portion connected to the flexible membrane; and the method further includes the step of inflating the inflatable portion by delivering an inflation medium into the inflatable portion.

20. The method of claim 17 or 18 wherein:

the providing step further provides an inflatable portion connected to the flexible membrane and having an outlet connected to the distal end of the shaft; and the method further includes the step of inflating the inflatable portion by delivering an inflation medium through the shaft and into the inflatable portion.

21. An apparatus kit for closing a wound with a suture having at least two ends, the apparatus comprising:

a suture having at least two ends;

a suture receiver having an inflatable membrane connected to an inflation port, the suture receiver insertable through the wound and into a body cavity underlying the wound;

a needle means for carrying the ends of the suture through tissue surrounding the wound and to the suture receiver;

anchoring means attached to the ends of the suture, for anchoring the suture ends to the suture receiver while within the body cavity;

withdrawing means for withdrawing the suture receiver with the anchor means and the ends attached thereto through the wound and out of the body cavity.

* * * * *